US010898156B2

(12) United States Patent
Nebosis et al.

(10) Patent No.: US 10,898,156 B2
(45) Date of Patent: Jan. 26, 2021

(54) RADIATION IMAGE CAPTURING SYSTEM AND METHOD

(71) Applicant: Agfa HealthCare NV, Mortsel (BE)

(72) Inventors: Rainer Nebosis, Munich (DE);
Vladimir Zemanek, Neubiberg (DE);
Johannes Hoelzl, Grasbrunn (DE);
Georg Reiser, Munich (DE); Roland Reuter, Kolbermoor (DE)

(73) Assignee: AGFA Healthcare NV, Mortsel (BE)

( * ) Notice: Subject to any disclaimer, the term of this patent is extended or adjusted under 35 U.S.C. 154(b) by 31 days.

(21) Appl. No.: 16/094,290

(22) PCT Filed: Mar. 30, 2017

(86) PCT No.: PCT/EP2017/057523
§ 371 (c)(1),
(2) Date: Oct. 17, 2018

(87) PCT Pub. No.: WO2017/182248
PCT Pub. Date: Oct. 26, 2017

(65) Prior Publication Data
US 2019/0125292 A1 May 2, 2019

(30) Foreign Application Priority Data
Apr. 19, 2016 (EP) ..................................... 16165953

(51) Int. Cl.
*H05G 1/10* (2006.01)
*A61B 6/00* (2006.01)
*A61B 6/08* (2006.01)

(52) U.S. Cl.
CPC ................ *A61B 6/547* (2013.01); *A61B 6/08* (2013.01); *A61B 6/4405* (2013.01);
(Continued)

(58) Field of Classification Search
CPC ... A61B 6/4291; A61B 6/4405; A61B 6/4452; A61B 6/587; A61B 6/547; A61B 6/4233;
(Continued)

(56) References Cited

U.S. PATENT DOCUMENTS 7,581,884 B1 9/2009 Barnes et al.
2012/0230473 A1 9/2012 Stagnitto et al.
(Continued)

FOREIGN PATENT DOCUMENTS

JP 2011-004869 A 1/2011

OTHER PUBLICATIONS

Official Communication issued in International Patent Application No. PCT/EP2017/057523, dated Jun. 7, 2017.

*Primary Examiner* — Irakli Kiknadze
(74) *Attorney, Agent, or Firm* — Stinson LLP

(57) ABSTRACT

A radiation image capturing system includes a processing unit that determines at least three distances between at least one first distance sensor provided at a radiation generation unit and at least three second distance sensors provided at a detection unit based on one or more signals emitted by the first distance sensor, and that determines an orientation of the radiation generation unit and the detection unit relative to each other based on inclination information provided by a first sensor unit provided at the radiation generation unit and a second sensor unit provided at the detection unit. Alternatively, the processing unit determines distances between at least three first distance sensors provided at the radiation generation unit and at least three second distance sensors provided at the detection unit based on signals emitted by the at least three first distance sensors to determine an orientation of the radiation generation unit and the detection unit relative to each other.

10 Claims, 5 Drawing Sheets

(52) U.S. Cl.
CPC ............ *A61B 6/4452* (2013.01); *A61B 6/467* (2013.01); *A61B 6/587* (2013.01); *A61B 6/588* (2013.01)

(58) Field of Classification Search
CPC ... A61B 6/4283; A61B 6/4441; A61B 6/4464; A61B 6/56; A61B 6/032; A61B 6/107; A61B 6/14; A61B 6/487; A61B 2034/2048; A61B 6/5258; A61B 2562/0223; A61B 6/08; A61B 6/467; A61B 6/4028; A61B 6/4417; A61B 6/461; A61B 6/588; G01B 7/30; G01B 11/002; G01T 1/2928; G01T 1/17; G01N 23/04; G06T 7/0004; H03M 13/1102; H03M 13/353; G01R 33/0206; G01P 13/025; G01S 17/66; G01S 3/783; G01S 3/786; G01S 5/163; G06K 9/6263; G06K 9/62; G06K 9/6262; G06N 20/00; G06N 3/006; G06N 3/02; G06N 3/0445; G06N 3/0454; G06N 3/0472; G06N 3/084; G06N 3/088; G06N 3/126; G06N 5/046; G06N 7/005; G06N 20/10; G06N 20/20; G06N 3/0427; G06N 3/0436; G06N 3/049; G06N 3/086
USPC .................................... 378/62, 95, 205, 207
See application file for complete search history.

(56) References Cited

U.S. PATENT DOCUMENTS

2014/0341349 A1  11/2014  Lalena et al.
2014/0376700 A1  12/2014  Kwak et al.

RADIATION IMAGE CAPTURING SYSTEM AND METHOD

CROSS REFERENCE TO RELATED APPLICATIONS

This application is a 371 National Stage Application of PCT/EP2017/057523, filed Mar. 30, 2017. This application claims the benefit of European Application No. 16165953.7, filed Apr. 19, 2016, which is incorporated by reference herein in its entirety.

BACKGROUND OF THE INVENTION

1. Field of the Invention

The present invention relates to a radiation image capturing system and a method for operating a radiation image capturing system.

2. Description of the Related Art

In medical imaging, in particular X-ray imaging, radiation generated by a radiation generation unit is, after transmission and/or scattering by an object, detected by a detection unit in a spatially resolved manner. In order to provide medical images with high diagnostic value, it is usually necessary to adjust the position of the radiation generation unit and the detection unit relative to each other. However, in order to be able to adjust the position, in particular the so-called source-to-image distance (SID), of the radiation generation unit and the detection unit properly, the actual position or distance of the radiation generation unit and/or detection unit has to be determined.

SUMMARY OF THE INVENTION

Preferred embodiments of the invention provide a radiation image capturing system and an according method for operating a radiation image capturing system which allow for a precise determination of a position, in particular a distance, and/or an orientation of the radiation generation unit and the detection unit relative to each other.

These advantages and benefits are achieved by the system and method defined below.

A radiation image capturing system according to a first aspect of the invention comprises a radiation generation unit configured to generate X-ray radiation, a carriage on which the radiation generation unit is mounted, wherein the carriage is a mobile carriage and/or the radiation generation unit is movably mounted on the carriage, and at least one detection unit configured to capture a radiation image based on X-ray radiation generated by the radiation generation unit and transmitted and/or reflected by an object. Further, the system comprises at least one first distance sensor provided at the radiation generation unit and/or at a fixed position relative to the radiation generation unit, and at least three second distance sensors provided at the detection unit, wherein the at least one first distance sensor is configured to emit or receive one or more signals, and each of the at least three second distance sensors is configured to receive or emit, respectively, the one or more signals emitted or received, respectively, by the at least one first distance sensor. The system further comprises a first sensor unit provided at the radiation generation unit, the first sensor unit being configured to provide inclination information regarding an inclination of the radiation generation unit, and a second sensor unit provided at the detection unit, the second sensor unit being configured to provide inclination information regarding an inclination of the detection unit. A processing unit is configured to determine at least three distances between the at least one first distance sensor provided at the radiation generation unit and the at least three second distance sensors provided at the detection unit based on the one or more emitted and received signals, and to determine an orientation of the radiation generation unit and detection unit relative to each other based on the inclination information provided by the first and second sensor unit, and to further determine a position and/or a distance of the radiation generation unit and the detection unit relative to each other based on the determined distances between the at least one first distance sensor and the at least three second distance sensors and on the determined orientation of the radiation generation unit and the detection unit relative to each other.

A method according to a second aspect of the invention allows for operating a radiation image capturing system, which comprises a radiation generation unit configured to generate X-ray radiation, a carriage on which the radiation generation unit is mounted, wherein the carriage is a mobile carriage and/or the radiation generation unit is movably mounted on the carriage, at least one detection unit configured to capture a radiation image based on X-ray radiation generated by the radiation generation unit and transmitted and/or reflected by an object, at least one first distance sensor provided at a fixed position relative to the radiation generation unit, at least three second distance sensors provided at the detection unit, a first sensor unit provided at the radiation generation unit, and a second sensor unit provided at the detection unit, wherein the method comprises the following steps: emitting or receiving one or more signals by the at least one first distance sensor, and receiving or emitting, respectively, the one or more emitted or received, respectively, signals by each of the at least three second distance sensors, and detecting inclination information regarding an inclination of the radiation generation unit by the first sensor unit, and detecting inclination information regarding an inclination of the detection unit by the second sensor unit. The method further comprises the following steps: determining at least three distances between the at least one first distance sensor provided at the radiation generation unit and the at least three second distance sensors provided at the detection unit based on the one or more emitted and received signals, determining an orientation of the radiation generation unit and detection unit relative to each other based on the inclination information detected by the first and second sensor unit, and determining a position and/or a distance of the radiation generation unit and the detection unit relative to each other based on the determined distances between the at least one first distance sensor and the at least three second distance sensors and on the determined orientation of the radiation generation unit and the detection unit relative to each other.

A radiation image capturing system according to a third aspect of the invention comprises a radiation generation unit configured to generate X-ray radiation, a carriage on which the radiation generation unit is mounted, wherein the carriage is a mobile carriage and/or the radiation generation unit is movably mounted on the carriage, and at least one detection unit configured to capture a radiation image based on X-ray radiation generated by the radiation generation unit and transmitted and/or reflected by an object. Further, the system comprises at least three first distance sensors, each provided at a fixed position relative to the radiation generation unit, and at least three second distance sensors provided at the detection unit, wherein the at least three first distance sensors are configured to emit or receive one or more signals, and each of the at least three second distance sensors is configured to receive or emit, respectively, the one or more signals emitted or received, respectively, by the at least three first distance sensors. The system further comprises a processing unit configured to determine distances between the at least three first distance sensors provided at the radiation generation unit and the at least three second distance sensors provided at the detection unit based on the one or more emitted and received signals, and further configured to determine an orientation of the radiation generation unit and detection unit relative to each other based on the distances between the at least three first distance sensors and the at least three second distance sensors. The processing unit is further configured to determine a position and/or a distance of the radiation generation unit and the detection unit relative to each other based on the determined distances between the at least three first distance sensors and the at least three second distance sensors, and on the determined orientation of the radiation generation unit and the detection unit relative to each other.

A method according to a fourth aspect of the invention allows for operating a radiation image capturing system, which comprises a radiation generation unit configured to generate X-ray radiation, a carriage on which the radiation generation unit is mounted, wherein the carriage is a mobile carriage and/or the radiation generation unit is movably mounted on the carriage, at least one detection unit configured to capture a radiation image based on X-ray radiation generated by the radiation generation unit and transmitted and/or reflected by an object, at least three first distance sensors, each provided at a fixed position relative to the radiation generation unit, and at least three second distance sensors provided at the detection unit, wherein the method comprises the following steps: emitting or receiving one or more signals by the at least three first distance sensors, and receiving or emitting, respectively, the one or more emitted or received signals, respectively, by each of the at least three second distance sensors, and determining distances between the at least three first distance sensors provided at the radiation generation unit and the at least three second distance sensors provided at the detection unit based on the one or more emitted and received signals. The method further comprises the steps of determining an orientation of the radiation generation unit and detection unit relative to each other based on distances between the at least three first distance sensors and the at least three second distance sensors, and determining a position and/or a distance of the radiation generation unit and the detection unit relative to each other based on the determined distances between the at least three first distance sensors and the at least three second distance sensors, and on the determined orientation of the radiation generation unit and the detection unit relative to each other.

The aforementioned aspects of the invention are based on the common approach to determine at least one position, in particular at least one distance, and/or orientation of the radiation generation unit and the detection unit relative to each other based on distances between at least one first distance sensor, which is provided at the radiation generation unit, and at least three second distance sensors, which are provided at the detection unit, and by considering an orientation of the radiation generation unit and the detection unit relative to each other. The orientation is determined based either on inclination information provided by separate sensors (first and second aspect of the invention) or on the determined distances between the distance sensors (third and fourth aspect of the invention).

To this end, at least one first distance sensor is provided at a fixed position relative to the radiation generation unit, whereby the distance of the at least one first distance sensor to the radiation generation unit and/or a particular element of the radiation generation unit, e.g. an aperture, a collimator or the like, is predefined. Further, the at least three second distance sensors are provided at the detection unit, in particular at or close to three edges and/or corners of the detection unit. The at least one first distance sensor is configured to emit one or more signals, and the at least three second distance sensors are configured to receive the one or more signals emitted by the at least one first distance sensor. Alternatively, the at least three second distance sensors are configured to emit signals and the at least one first distance sensor is configured to receive the signals emitted by the at least three second distance sensors. In either case, the processing unit is configured to determine at least three distances between a first distance sensor and the at least three second distance sensors based on and/or by considering the one or more emitted and subsequently received signals in case only one first distance sensor is provided. If three or more first distance sensors are provided, the processing unit is configured to determine distances between the at least three first distance sensors and the at least three second distance sensors. Moreover, the processing unit is configured to determine the orientation, in particular the inclination, of the radiation generation unit and the detection unit relative to each other by either considering signals of a first inclination sensor unit, which is provided at the radiation generation unit, and signals of a second inclination sensor unit which is provided at the detection unit, or by considering the distances between the at least three first distance sensors and the at least three second distance sensors. The processing unit is configured to determine the position and/or the distance of the radiation generation unit and detection unit relative to each other by combining the determined orientation of the radiation generation unit and the detection unit relative to each other with the measured or determined distances between the at least one first distance sensor and the at least three second distance sensors.

In this way, the position, in particular the distance, and/or the orientation of the radiation generation unit and the detection unit relative to each other are determined very precisely.

Preferably, the processing unit is configured to determine whether the radiation generation unit and the detection unit are in an aligned, in particular a predetermined, orientation and/or position relative to each other, based on the determined inclination of the radiation generation unit and the detection unit relative to each other and the determined position and/or distance of the radiation generation unit and the detection unit relative to each other.

In the sense of the present invention, the terms "aligned orientation", "aligned position", "predetermined orientation" and "predetermined position" preferably relate to an orientation, in particular an inclination, and/or a position, in particular a distance, of the radiation generation unit and detection unit relative to each other, where requirements for capturing a high quality radiation image of the object to be imaged are met. In particular, the terms correspond to an orientation, in particular an inclination, and/or a position, in particular a distance, of the radiation generation unit and detection unit relative to each other, where radiation emitted by the radiation generation unit and transmitted and/or scattered by the object impinges essentially orthogonally or under a predefined angle close to 90° on the detection unit, in particular the area of the detection unit which is sensitive to the radiation, and/or where the distance between the radiation generation unit and the detection unit corresponds to a predefined distance, in particular a source-to-image-distance (SID), between radiation generation unit and detection unit, wherein the predefined distance may be dependent on the collimation of the radiation and/or the requirements of the image to be captured.

Preferably, the carriage may be a mobile carriage which is configured to be moved or positioned relative to the object to be imaged and/or relative to the detection unit. To that end, the mobile carriage preferably comprises wheels, in particular at least one caster wheel and/or at least two omnidirectional wheels which are configured to allow for movement of the carriage in all directions on a two-dimensional plane, in particular essentially parallel to the floor. By this means, the mobile carriage is particularly maneuverable and the radiation image capturing system may be easily employed at a patient's bedside, in particular in environments where space is limited.

Alternatively or additionally, the detection unit is configured to be moved or positioned relative to the object, the radiation generation unit and/or the carriage, in particular the mobile carriage. In particular, the detection unit is provided as a portable detection unit. By this means, the imaging geometry, i.e. the position and orientation of the detection unit and the object to be imaged relative to each other, can be easily adjusted or adapted, in particular to the requirements of the image or imaging procedure. Further, the orientation and/or position of the detection unit, in particular relative to the orientation and/or position of the radiation generation unit, can be easily changed, in particular into an aligned orientation and/or position.

In a preferred embodiment, each of the first and second sensor unit comprises at least one acceleration sensor configured to provide first inclination information concerning an acceleration of the acceleration sensor with respect to three spatial directions, and/or at least one gyroscope sensor configured to provide second inclination information concerning an orientation of the gyroscope sensor with respect to three spatial directions, and/or at least one magnetic field sensor configured to provide third inclination information regarding a magnetic field surrounding the magnetic field sensor with respect to three spatial directions. Further, the processing unit is configured to determine the orientation of the radiation generation unit and the detection unit relative to each other based on at least one of the first, second and third inclination information provided by first and second sensor unit. In this embodiment, a first tilt sensor unit is integrated in the radiation generation unit and a second tilt sensor unit is integrated in the detection unit, wherein each one of the first and second tilt sensor unit comprises a 3D or 3-axis acceleration sensor and/or a 3D or 3-axis gyroscopic sensor and/or a 3D or 3-axis magnetic field sensor. Because each of the first and second sensor unit comprises three different sensors capturing information with respect to three dimensions or axis, each one of the first and second sensor unit may be regarded as a "9-axis" sensor unit. The acceleration sensor can measure the absolute tilt of the respective component, i.e. the radiation generation unit or detection unit, with respect to the gravity vector, if the component does not move. If the component moves, additional acceleration forces may influence the result. The gyroscopic sensor measures a relative tilt only, but independently of possible acceleration forces. Further, the magnetic field sensor signals also allows for an absolute tilt measurement, but can be influenced by magnetic fields produced by devices (e.g. motors) close by the respective sensor. By combing the signals of the acceleration sensors with the signals of the gyroscope and/or magnetic sensors (static field), the limitations of each sensor type are advantageously overcome so that the absolute and/or relative orientation of the radiation generation unit and/or the detection unit can be determined very precisely.

In particular, the processing unit is configured to determine, based on at least one of the first, second and third inclination information provided by the first and second sensor unit, whether the radiation generation unit and the detection unit are in an aligned, in particular a predetermined, orientation relative to each other. Preferably, the processing unit is configured to enable capturing of radiation images only if the radiation generation unit and the detection unit are in an aligned orientation relative to each other. Preferably, the processing unit is configured to issue an information and/or signal to the user whether the system is aligned and therefore ready for capturing radiation images or the radiation generation unit and/or the detection unit still have to be positioned and/or tilted in order to achieve an aligned position.

In another preferred embodiment, the first and second sensor unit each comprises the at least one acceleration sensor, the at least one gyroscope sensor and the at least one magnetic field sensor. Further, the processing unit is configured to determine the orientation of the radiation generation unit and the detection unit relative to each other based on the first, second and third inclination information provided by first and second sensor unit. By this means, each of the first and second sensor unit comprises three different sensor types providing complimentary information regarding the orientation, in particular inclination, of the radiation generation unit and the detection unit. Preferably, the processing unit is configured to determine whether the components are in an aligned, in particular in a predetermined, orientation, based on the combination of the complimentary first, second and third inclination information provided by the first and second sensor unit such that the resulting orientation and/or position information is particularly precise and reliable.

In another preferred embodiment, the processing unit is configured to determine the position and/or the distance of the radiation generation unit and the detection unit relative to each other based on a distance between the at least one first distance sensor and a predefined position at the detection unit, in particular a center of an X-ray sensitive area of the detection unit, wherein the processing unit is configured to determine the distance between the at least one first distance sensor and the predefined position at the detection unit based on the determined distances between the first distance sensor and the at least three second distance sensors, and on the determined orientation of the radiation generation unit and the detection unit relative to each other. In particular, the processing unit is configured to process the determined distances between the first distance sensor and the at least three second distance sensors by considering the determined orientation of the radiation generation unit and the detection unit relative to each other, in particular such that an alignment of the detection unit relative to the radiation generation unit and/or the carriage is taken into account. By this means, the determination of the position and/or distance of the radiation generation unit and the detection unit relative to each other is particularly precise.

In another preferred embodiment, the processing unit is configured to determine the distance between the at least one first distance sensor and the predefined position at the detection unit based on information regarding a transformation, in particular a rotation, of coordinates of the at least three second distance sensors relative to the predefined position at the detection unit into coordinates relative to the at least one first distance sensor. Preferably, the positions of the at least three second distance sensors relative to the predefined position at the detection unit are given by coordinates, in particular vectors, in particular in a coordinate system having its origin in the predefined position at the detection unit. Preferably, the processing unit is configured to determine the distance between the at least one first distance sensor and the at least three second distance sensors by constructing a transformation matrix, in particular a rotation matrix, which, upon application to the vectors giving the positions of the at least three second distance sensors relative to the predefined position at the detection unit, aligns the coordinate system having its origin in the predefined position at the detection unit with a coordinate system having its origin in the at least one first distance sensor. By this means, the determination of the distance between the at least first distance sensor and the predefined position at the detector unit and/or the position, in particular the distance, of the radiation generation unit and the detection unit relative to each other is particularly precise and easy to achieve.

In another preferred embodiment, the one or more signals emitted and received by the at least one first distance sensor or the at least three second distance sensors, respectively, are ultrasound signals or magnetic signals, in particular a magnetic flux, or electromagnetic signals, in particular light.

In one embodiment, the at least three second distance sensors are provided close to an edge and/or corner of the detection unit so that the detection unit can be positioned beneath or behind a patient such that there is no object, in particular no part of the patient, between the at least three second distance sensors provided at the detection unit and the at least one first distance sensor provided at the radiation generation unit, allowing for a reliable transmission of the one or more signals between the at least one first distance sensor and the at least three second distance sensors. This embodiment is particularly preferred if the one or more signals emitted and received by the at least one first distance sensor or the at least three second distance sensors, respectively, are ultrasound signals or electromagnetic signals, in particular light.

Preferably, the at least one first distance sensor or the at least three second distance sensors are configured to generate a sequence of short pulses or a time varying signal, e.g. a sinusoidal signal. Further preferably, the processing unit is configured to analyze the pulse sequence or time varying signal received by the at least three second distance sensors or the at least one first distance sensor, respectively, in particular by performing a run time measurement, i.e. a time-of-flight analysis, and/or a three-dimensional measurement of the signal amplitude, in particular of the magnetic flux, and/or a three-dimensional camera pattern recognition, in particular with light, allowing for a precise determination of the distance, in particular the SID, between radiation generation unit and detection unit and/or between the at least one first distance sensor and the at least three second distance sensors.

In yet another preferred embodiment, the radiation image capturing system is configured to retain the radiation generation unit in a first reference position and the detection unit in a second reference position. Preferably, the first and/or second reference position is a transport position, i.e. a position in which the radiation generation unit and/or the detection unit is retained when the radiation image capturing system is or shall be transported. The first and second reference positions are positions in which the position and/or the orientation of the radiation generation unit and the detection unit are defined. Accordingly, when the radiation generation unit is in the first reference position and/or the detection unit is in the second reference position, the sensors of the first and/or second sensor unit regarding the orientation and/or position of the radiation generation unit or the detection unit, respectively, can be calibrated.

Alternatively or additionally, the first and/or second reference position is an idle position, i.e. a position in which the radiation generation unit and/or the detection unit is retained when the radiation capturing system is not in use.

Moreover, it is preferred that the radiation generation unit and/or detection unit comprise a first and/or second reference sensor, respectively, configured to determine whether the radiation generation unit and/or detection unit is in its respective reference position. In particular, the first and/or second reference sensor is configured to send a first notification signal to the processing unit if the radiation generation unit and/or detection unit is removed from its respective reference position. Preferably, the processing unit is configured to return the radiation image capturing system from an idle state, i.e. a stand-by state, to an operational state upon receipt of the first notification signal from the first and/or second reference sensor.

Moreover, it is preferred that the radiation generation unit and/or the detection unit are retained in the first and second reference position with a small mechanical tolerance so that an initial orientation and/or position of the radiation generation unit and the detection unit relative to each other is defined with high accuracy. In particular, the radiation generation unit and/or the detection unit are retained in its respective reference position such that jiggling and/or slippage of the radiation generation unit and/or detection unit is prevented, whereby a particularly precise reference positioning and safe accommodation in the first and/or second reference position, in particular during transport of the system or parts thereof, is achieved.

According to another preferred embodiment, the radiation image capturing system comprises a first retaining element configured to accommodate the radiation generation unit in the first reference position and/or a second retaining element, in particular a receptacle, configured to accommodate the detection unit in the second reference position. Preferably, by means of the first and/or second retaining element, the radiation generation unit and/or the detection unit can be accommodated, in particular fixed, in the first and/or second reference position. This allows for a particularly reliable accommodation and precise alignment, i.e. positioning and/or orientation, of the radiation generation unit and/or the detection unit in the first and/or second reference position, so that the sensors of the first and/or second sensor unit can be calibrated with particularly high reliability. Preferably, a calibration of the first and/or second sensor unit is performed when the system is in an idle state, e.g. during transport of the system where no X-rays are recorded, in which the radiation generation unit and/or the detection unit are in the first and second reference position, respectively.

In another preferred embodiment, the processing unit is configured to determine the orientation of the radiation generation unit and the detection unit relative to each other by further considering inclination information, in particular first, second and third inclination information captured by the accelerometer, gyroscope and magnetic field sensor, respectively, provided by the first sensor unit while the radiation generation unit is retained in the first reference position. Alternatively and/or additionally, the processing unit is further configured to consider inclination information, in particular first, second and third inclination information captured by the accelerometer, gyroscope and magnetic field sensor, respectively, provided by the second sensor unit while the detection unit is retained in the second reference position. By capturing the first, second and third information provided by either of the first and second sensor unit while the radiation generation unit and/or the detection unit is in the first or second reference position, respectively, initial values or calibration values of the corresponding sensors are obtained. By considering the calibration values of the accelerometer sensor, the gyroscope sensor and the magnetic field sensor of the first and/or second sensor unit as well as the first, second and third information captured by the accelerometer sensor, the gyroscope sensor and the magnetic field sensor of the first and/or second sensor unit while the radiation generation unit and/or the detection unit are in use, e.g. during or immediately prior to or after taking an X-ray, a particularly reliable and precise determination of the orientation and/or position of the radiation generation unit and the detection unit relative to each other is obtained.

The first and/or second reference sensor is or are preferably configured to generate a second notification signal when the radiation generation unit and/or the detection unit is or are brought into the first and/or second reference position after having been outside the first and/or second reference position.

Moreover, the control unit is preferably configured to perform a calibration procedure for calibrating the first and/or the second sensor unit if the radiation generation unit and/or the detection unit are in the first and/or the second reference position, in particular upon receiving the second notification signal from the first and/or the second reference sensor.

In the sense of the present invention the term "calibrating" and/or "calibration procedure" refers to acquiring, and in particular storing, first, second and third information generated by the acceleration sensor, the gyroscope sensor and the magnetic field sensor, also referred to as "calibration values", of each of the first and the second sensor unit while the radiation generation unit and the detection unit is in the first and/or second reference position, respectively. When determining a position and/or orientation of the radiation generation unit and/or the detection unit, in particular relative to each other, at a later point in time, currently captured first, second and third information can be compared and/or related to the stored first, second and third information generated during calibration. By considering the calibration values obtained in the calibration procedure, any later position and/or orientation of the radiation generation unit and/or the detection unit can be determined relative to the first and/or the second reference position by tracking the orientation and/or position of the radiation generation unit and/or the detection unit after their removal from the first or second reference position, respectively. In particular, by following the change of the orientation and/or position, in particular a change in inclination and/or an acceleration, of either or both of the radiation generation unit and the detection unit upon removal from the first and/or second reference position, the current position and/or orientation of the radiation generation unit and/or the detection unit can be determined with particularly high precision.

Preferably, the processing unit comprises a ring buffer which is configured to store at least 18 calibration values, wherein the at least 18 calibration values correspond to first, second and third information with respect to three spatial directions of the acceleration sensor, gyroscope sensor and magnetic field sensor, respectively, of each of the first and second sensor unit. Alternatively or additionally, the processing unit is configured to determine the at least 18 calibration values while the radiation generation unit and the detection unit are retained in the first and second reference position, respectively, in particular upon receipt of the second notification signal, and to store the calibration values in a memory, in particular the ring buffer.

Moreover, it is preferred that the processing unit is configured to perform the calibration procedure in a continuous manner, such that calibration values, i.e. first, second and third information from each of the first and second sensor unit, are continuously captured and stored into the ring buffer. In particular, the processing unit is configured to replace the calibration values stored in the ring buffer with the most recently captured and/or determined calibration values, whereby the calibration values in the ring buffer are always kept up to date.

Further, the processing unit is preferably configured to terminate the calibration procedure upon receiving a first notification signal, e.g. upon removal of the radiation generation unit and/or the detection unit from the first and/or second reference position. Preferably, in a following determination of the position and/or orientation of the radiation generation unit and the detection unit relative to each other, the processing unit is configured to consider the at least 18 most recently captured and/or determined calibration values stored in the ring buffer in addition to first, second and third information generated by the acceleration sensor, gyroscope sensor and magnetic field sensor of both first and second sensor unit. By this means, only a very short period of time between usage of the system and the last calibration or calibration procedure elapses so that the orientation and/or position of the radiation generation unit and detection unit relative to each other can be determined with particularly high accuracy.

According to another preferred embodiment, the processing unit is configured to determine the orientation and/or position of the radiation generation unit and the detection unit relative to each other by further considering first information captured by the accelerometer sensor of the first sensor unit while the radiation generation unit is retained in the first reference position and the carriage is not accelerated, and/or first information captured by the accelerometer sensor of the second sensor unit while the detection unit is retained in the second reference position and the carriage is not accelerated. By this means, the acceleration measured by the acceleration sensors is not influenced by a variation in acceleration due to movement and only reflects constant acceleration due to gravity. Accordingly, the obtained first information relates to an absolute inclination or tilt information, wherein the first information captured by the acceleration sensor of the first and/or second sensor unit provides information regarding the orientation of the first and/or second sensor unit or the radiation generation unit and/or the detection unit, respectively, relative to the gravity vector.

Moreover, in another preferred embodiment the processing unit is configured to determine whether the radiation image capturing system is in a safe state, and in the positive, to perform the calibration procedure irrespective of whether the radiation generation unit and/or the detection unit is or are retained in the first and/or second reference position. In the sense of the present invention, a "safe state" is a state in which no component of the radiation image capturing system, in particular neither radiation generation unit nor detection unit, is accelerated. Preferably, the processing unit is configured to determine whether the radiation image capturing system is in a safe state by analyzing whether the first information, i.e. the acceleration values provided by the acceleration sensors of each of the first and second sensor unit, equals the gravity vector.

According to another preferred embodiment, the radiation image capturing system comprises an output unit configured to visually and/or acoustically output information to a user, wherein the processing unit is configured to determine, based on the orientation and/or position of the radiation generation unit and the detection unit relative to each other, whether the radiation generation unit and the detection unit are in an aligned orientation and/or position relative to each other and, in the negative, to determine positioning information on how the radiation generation unit and/or the detection unit has or have to be moved in order to be in an aligned orientation and/or position relative to each other, and to control the output unit to output the determined positioning information. The positioning information is determined based on the precisely determined orientation and/or position of the radiation generation unit and the detection unit relative to each other. Accordingly, the outputted positioning information enables the user to precisely position the radiation generation unit and/or the detection unit in an aligned orientation and/or position relative to each other.

Preferably, the output unit is provided at the radiation generation unit or in vicinity of the radiation generation unit. This enables the user to easily and comfortably perceive the positioning information prior to and/or while positioning the radiation generation unit. Alternatively or additionally, the output unit is provided at the carriage. This allows an easy and comfortable perception of the positioning information in cases where the carriage is moved in order to bring the radiation generation unit and the detection unit into an aligned orientation and/or position relative to each other.

Preferably, the processing unit is configured to determine whether the radiation generation unit and the detection unit are in an aligned orientation and/or position relative to each other based on first, second and third information of both first and second sensor unit and calibration values stored in the ring buffer and the determined distances between the at least one first distance sensor and the at least three second distance sensors.

Moreover, the processing unit is preferably configured to determine whether the radiation generation unit and the detection unit are in an aligned orientation and/or position relative to each other based on first, second and third information of both first and second sensor unit and calibration values stored in the ring buffer and the determined distances between the at least one first distance sensor and the at least three second distance sensors every 10 to 1000 ms.

Preferably, the radiation image capturing system comprises a positioning support unit configured to support positioning of the radiation generation unit relative to the detection unit. Preferably, the positioning support unit provides a motorized support, in particular by actuators, and/or hydraulic support of manually induced movement of the radiation generation unit and/or the detection unit by the user. By this means, the radiation generation unit and detection unit can be brought into an aligned orientation and/or position relative to each other based on the positioning information quickly and precisely, in particular without the necessity of the user exerting large forces.

Moreover, the position support unit preferably comprises position controls configured to allow an input of movement instructions by the user. In particular, the position controls enable the user to control the movement of radiation generation unit and/or detection unit, in particular their orientation and/or position, preferably relative to each other. Further preferably, the position controls are provided at the radiation generation unit or in the vicinity of the radiation generation unit. Alternatively or additionally, the controls are provided at the carriage. By this means, a particularly comfortable and precise positioning of the radiation generation unit can be performed.

According to another preferred embodiment, the radiation image capturing system comprises a positioning unit which is configured to position the radiation generation unit relative to the detection unit, wherein the processing unit is configured to determine, based on the orientation and/or position of the radiation generation unit and the detection unit relative to each other, whether the radiation generation unit and the detection unit are in an aligned orientation and/or position relative to each other and, in the negative, to determine positioning instructions for positioning the radiation generation unit in order to be in an aligned orientation and/or position relative to the detection unit, and to control the positioning unit to position the radiation generation unit in accordance with the positioning instructions. In particular, the positioning unit is configured to tilt and/or rotate and/or move the radiation generation unit in at least one spatial direction. By this means, a particularly precisely and reliably aligned orientation and/or position of the radiation generation unit and the detection unit relative to each other is achieved.

In another preferred embodiment, the radiation image capturing system comprises a handheld position tracker, at which a fourth sensor unit configured to capture fourth information regarding a position and/or orientation and/or movement of the handheld position tracker is provided, wherein the handheld position tracker is configured to be moved and/or tilted by a user, and the processing unit is configured to control the positioning unit to move the radiation generation unit based on the fourth information. Preferably, the handheld position tracker is configured to be grasped and/or grabbed by a hand or hands of the user. When the user performs a movement of his hand or hands while holding the handheld position tracker, the captured fourth information corresponds to the movement of the hand or hands, and the radiation generation unit preferably follows this movement. By this means, changing the position and/or orientation of the radiation generation unit, in particular relative to a patient and/or the detection unit, in particular bringing the radiation generation unit and the detection unit into an aligned position and/or orientation relative to each other, is accomplished in a particularly intuitive, fast and reliable way.

Preferably, the fourth sensor unit comprises one or more sensors configured to capture at least one of: an acceleration of the fourth sensor unit with respect to three spatial directions, an inclination of the fourth sensor unit with respect to three spatial directions, a magnetic field surrounding the fourth sensor unit with respect to three spatial directions. In particular, the fourth information corresponds to at least one of the acceleration of the fourth sensor unit, the inclination of the fourth sensor unit and the magnetic field surrounding the fourth sensor unit, and the processing unit is preferably configured to determine the movement of the handheld position tracker, at which the fourth sensor unit is provided, based on the fourth information.

Moreover, the processing unit is preferably configured to track, in particular to track changes of, the acceleration of the fourth sensor unit with respect to three spatial directions and/or the inclination of the fourth sensor unit with respect to three spatial directions and/or the magnetic field surrounding the fourth sensor unit with respect to three spatial directions over time. In this way, the movement, i.e. translation and/or tilt, of the handheld position tracker can be precisely determined.

In another preferred embodiment, the handheld position tracker comprises one or more tracking control elements for setting at least one tracking mode, and the processing unit is configured to control the positioning unit based on the fourth information and according to the tracking mode set by the one or more tracking control elements. Preferably, a first tracking control element activates, e.g. by pushing an activation button, the handheld position tracker, such that the processing unit controls the positioning unit to move, i.e. translate and/or tilt, the radiation generation unit based on the fourth information, as described above. Further preferably, the first tracking control element may also deactivate the handheld position tracker, e.g. by pushing the activation button again. Alternatively or additionally, the processing unit is configured to determine the orientation and/or position of the handheld position tracker, in particular relative to the orientation and/or position of the radiation generation unit, preferably by considering fourth information captured by the fourth sensor unit, provided at the handheld position tracker, and by considering first, second and third information captured by the first sensor unit, provided at the radiation generation unit. A second tracking control element activates a second tracking mode, in which the processing unit controls the positioning unit to move the radiation generation unit into a predefined position relative to the handheld position tracker. By this means, the position tracker may be used to mark a certain position, e.g. a body part of the patient, which is to be imaged, wherein the radiation generation unit is positioned automatically in an orientation and/or position relative to the marked position such that high quality radiation images may be reliably captured.

Further advantages, features and examples of the present invention will be apparent from the following description of following figures:

DETAILED DESCRIPTION OF THE PREFERRED EMBODIMENTS

Figure 1:
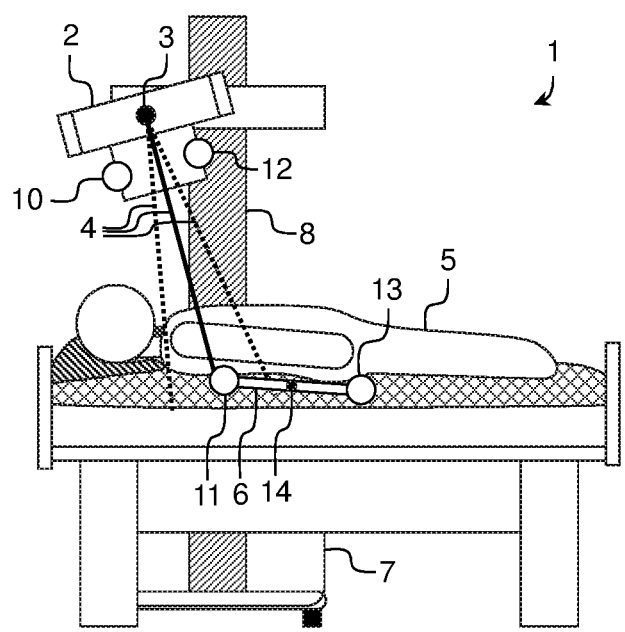
FIG. 1 shows a front view of an example of a radiation image capturing system at a patient's bedside.

FIG. 1 shows a front view of an example of a radiation image capturing system 1 which is located at a patient's bedside. A radiation generation unit 2 comprises a radiation source 3, also referred to as X-ray tube, which is configured to generate X-ray radiation 4. Below the radiation generation unit 2, the patient 5 to be examined lies on a bed. X-ray radiation 4 transmits through the patient 5 and impinges on a detection unit 6, which is configured to detect the radiation, e.g. by converting it into electrical signals by means of a solid-state detector, by storing it in a storage phosphor sheet or by recording it on a photographic film. The detection unit 6 is portable, such that it can be easily positioned into a desired orientation and/or position beneath or behind the patient 5.

In the example shown in FIG. 1, the radiation generation unit 2 and the detection unit 6 are not in an aligned orientation and/or position relative to each other, because the X-ray radiation 4, in particular the central beam, generated by the radiation source 3 does not impinge orthogonally on the detection unit 2 and illuminates only a part of the sensitive area of the detection unit 6. Further, the X-ray radiation 4, in particular the X-ray radiation cone, is not centered on the detection unit 2, i.e. the center beam of the X-ray radiation 4 does not coincide with a predetermined position 14 at, i.e. the center of, the detection unit 2. For the sake of completeness it is pointed out that, in some X-ray exams, an orthogonal center beam of the X-ray radiation 4 is not necessarily required. However, the center beam should correspond more or less with the center of the detection unit 2.

In order to bring the radiation generation unit 2 and the detection unit 6 in an aligned position and/or orientation relative to each other, the radiation generation unit 2 is movably mounted on a carriage 7, in particular on a column 8 of the carriage 7, such that it can be translated and/or rotated relative to the carriage 7 and/or the column 8 until the radiation generation unit 2 and the detection unit 6 are properly aligned relative to each other, e.g. such that the center beam of the X-ray radiation 4 impinges on the detection unit 6 with a pre-specified angle of incidence, e.g. orthogonally, and/or the beam cone of the X-ray radiation 4 illuminates a pre-specified area of the detection unit 6. Preferably, the radiation generation unit 2 and the detection unit 6 can be aligned such that essentially all of the X-ray radiation 4 emitted by the radiation generation unit 2 is detected by the detection unit 6.

The radiation image capturing system 1 comprises a first sensor unit 10, which is provided at the radiation generation unit 2, in particular mounted at a housing of the radiation generation unit 2. The first sensor unit 10 is configured to provide information on the orientation and/or the position of the radiation generation unit 2, in particular on its inclination.

Moreover, a second sensor unit 11 is provided at the detection unit 6. The second sensor unit 11 is configured to provide information on the orientation and/or the position of the detection unit 6, in particular on its inclination. By combining the information provided by the first sensor unit 10 and the information provided by the second sensor unit 11, an orientation and/or a position of the radiation generation unit 2 and the detection unit 6 relative to each other can be determined as explained further below.

Preferably, the system 1 further comprises a transmitter 12, which is preferably provided at the radiation generation unit 2, in particular mounted at the housing of the radiation generation unit 2, and is configured to emit one or more signals, e.g. magnetic signals, electromagnetic signals, in particular light, and/or ultrasound signals. A receiver 13, which is provided at the detection unit 6, is configured to receive the one or more signals emitted by the transmitter 12. In an alternative embodiment (not shown), the transmitter 12 may be provided at the detection unit 6 and the receiver 13 may be provided at the radiation generation unit 2. Based on the one or more signals received by the receiver 13, a position and/or a distance of the radiation generation unit 2 and the detection unit 6 relative to each other, in particular the source-to-image distance (SID) of the radiation source 3 to a predefined position 14 at the detection unit 6, can be determined as explained further below.

Figure 2:
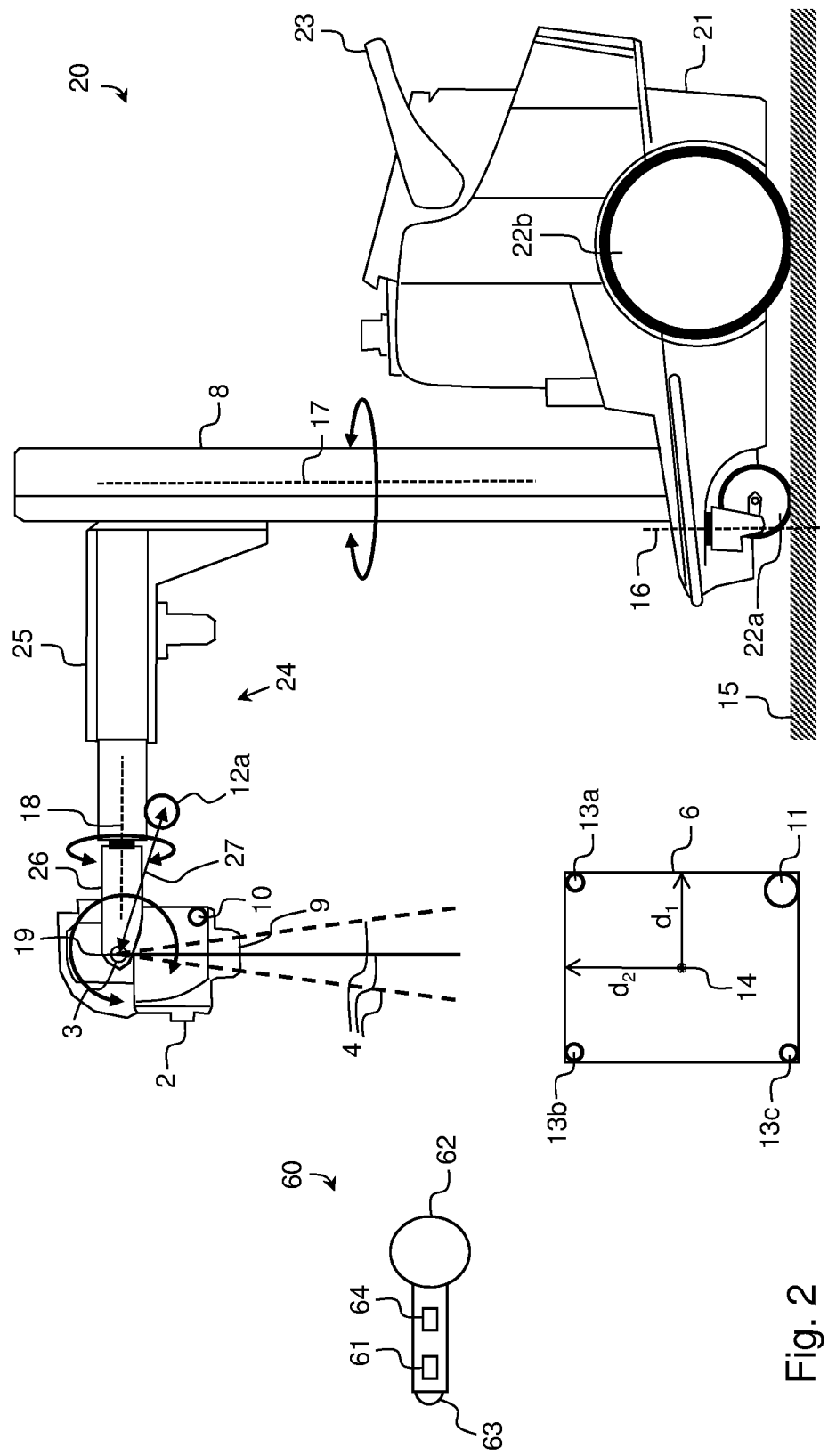
FIG. 2 shows a side view of another example of a radiation image capturing system.

FIG. 2 shows a side view of another example of a radiation image capturing system 20 comprising a mobile carriage 21 which is equipped with wheels 22a and 22b by which the carriage 21 can be moved across the floor 15. Preferably, first wheels 22a are designed as caster wheels which are configured to be rotated around a vertical axis 16 in order to provide high maneuverability of the carriage 21. Alternatively or additionally, second wheels 22b are designed as drive wheels 22b which are preferably coupled to a driving means, e.g. a motor, which is configured to drive the second wheels 22b.

Preferably, the carriage 21 comprises a handle 23 which can be actuated and/or grasped by a user to move, in particular to push and/or maneuver, the carriage 21.

On the carriage 21 a vertical column 8 is mounted, which is configured to be rotated around a first rotation axis 17, as indicated by a curved arrow around the column 8. On the column 8 a tube arm 24 is mounted at the distal end of which a radiation generation unit 2 is movably mounted.

The tube arm 24 comprises a first arm element 25 and a second arm element 26, wherein the second arm element 26 is rotatably mounted on the first arm element 25 such that it can be rotated around a second rotation axis 18 as indicated by a curved arrow around the second arm element 26. Further, the radiation generation unit 2 is rotatably mounted on the second arm element 26 such that it can be rotated around a third rotation axis 19 which is perpendicular to the image plane of FIG. 2. The movement of the radiation generation unit 2 upon a rotation around the third rotation axis 19 is indicated by a curved arrow around the third rotation axis 19. As a result, the radiation generation unit 2 is movably mounted on the first arm element 25 by a gimbal joint, i.e. it can be rotated such that an aperture 9 of the X-ray radiation 4 generated by the radiation generation unit 2 can be directed in any desired direction.

In a preferred embodiment (not shown), the first arm element 25 movably mounted on the column 8 such that it can be translated upwards and/or downwards along the column 8 in order to adjust the height of the radiation generation unit 2 relative to the floor 15. Alternatively or additionally, the first arm element 25 is a telescopic arm element, i.e. a first part of the first arm element 25 can be retracted into a second part of the first arm element 25, such that the distance between the radiation generation unit 2 and the column 8, i.e. the length of the tube arm 24, can be adjusted.

By means of the embodiments described above, preferably in combination with the maneuverability of the mobile carriage 21, the user has a number of degrees of freedom to adjust the orientation and/or position of the radiation generation unit 2 relative to a patient and/or a detection unit 6. As a result, the radiation generation unit 2 and the detection unit 6 may be easily and reliably brought into a desired and/or an aligned orientation and/or position relative to each other.

Like in the example shown in FIG. 1, a first sensor unit 10, which determines information on an orientation and/or a position of the radiation generation unit 2, is mounted at the radiation generation unit 2, whereas a first distance sensor 12a, which is configured as a transmitter, is provided at the first arm element 25 in a fixed or predetermined distance 27 to the radiation source 3. This arrangement advantageously prevents or at least minimizes an influence on the inclination or position detection in the first sensor unit 10 by signals, e.g. magnetic, electromagnetic or ultrasound signals, emitted by the first distance sensor 12a.

In the embodiment shown in FIG. 2 three second distance sensors 13a, 13b, 13c, which are configured as receivers, are provided at three corners of the detection unit 6, in particular at positions [d1, d2, 0], [−d1, d2, 0], [−d1, −d2, 0] in a coordinate system having its origin in a predetermined position 14, e.g. a center position, at the detection unit 6 and the z-axis perpendicular to the image plane. Each of the three second distance sensors 13a, 13b, 13c is configured to receive the one or more signals emitted by the first distance sensor 12a.

In an alternative embodiment, each of the three second distance sensors 13a, 13b, 13c is configured to emit one or more signals, e.g. magnetic, electromagnetic or ultrasound signals, and the first distance sensor 12a is configured to receive the one or more emitted signals. Based on the one or more signals received by the second distance sensors 13a, 13b, 13c, the distances between the first distance sensor 12a and each of the three second distance sensors 13a, 13b, 13c can be precisely determined.

Preferably, the source-to-image distance (SID) between the radiation source 3 and the predetermined position 14 at the detection unit 6 is determined based on the determined distances between the first distance sensor 12a and each of the three second distance sensors 13a, 13b, 13c and the fixed or predetermined distance 27 between the first distance sensor 12a and the radiation source 3.

Preferably, the SID between the radiation source 3 and the predefined position 14 at the detection unit 6 is determined not only by considering the determined distances between the second distance sensors 13a, 13b, 13c and the first distance sensor 12a and/or the distance 27 between the first distance sensor 12a and the radiation source 3, but also by considering information on an orientation of the detection unit 6 and/or the radiation generation unit 2, which is provided by the second sensor unit 11 or first sensor unit 10, respectively, which is described in detail further below.

Preferably, the distance sensors 12a, 13a, 13b, 13c are designed as magnetic coils, in particular coil triads each comprising three coils having winding axes perpendicular to each other, such that by applying an alternating current to the first distance sensor 12a, which acts as a transmitter, magnetic flux signals are emitted which may be received by the second distance sensors 13a, 13b, 13c, which act as receivers, by measuring the respective voltage and/or current induced in the coils. for example, the distances between the first distance sensor 12a and the three second distance sensors 13a, 13b, 13c can be determined by summing up the squares of the induced currents/voltages. Alternatively or additionally, the distances between the first distance sensor 12a and the three distance sensors 13a, 13b, 13c can be determined based on the induced currents/voltages and a predetermined correction or calibration factor taking into account the non-ideality of the system.

Alternatively, the distance sensors 12a, 13a, 13b, 13c are designed as ultrasound transmitters and receivers, respectively, whereby the distance between the first distance sensor 12a and the three second distance sensors 13a, 13b, 13c can be calculated by a run time measurement of one or more ultrasound signals emitted by the first distance sensor 12a and received by the three second distance sensors 13a, 13b, 13c.

In another embodiment, the radiation image capturing system 1 as shown in FIG. 1 and/or the mobile radiation image capturing system 20 as shown in FIG. 2 comprises a handheld position tracker 60 configured to capture movement instructions, based on which the radiation generation unit 2 is oriented and/or positioned, in particular in an aligned position relative to the detection unit 6. The handheld position tracker 60 is designed to be grasped and/or grabbed by the user. Upon activation of the handheld position tracker 60, e.g. by pushing an activation button 61, a fourth sensor unit 62 provided at the handheld position tracker 60 captures fourth information regarding a position and/or inclination and/or movement of the handheld position tracker 60, i.e. position and/or inclination and/or movement information. As described in more detail further below, the radiation image capturing system 1 and/or the mobile radiation image capturing system 20 is configured to receive the fourth information transmitted by a tracking transmitter 63 provided at the handheld position tracker 60 and to position, i.e. to translate and/or to tilt, the radiation generation unit 2 according to the captured fourth information or information derived therefrom. The tracking transmitter 63 is preferably part of a wireless communication system, e.g. bluetooth or a wireless LAN.

Preferably, the radiation generation unit 2 is moved, i.e. translated and/or tilt, in accordance with the movement of the handheld position tracker 60. That is, the radiation generation unit 2 follows the motion of the user's hand(s) holding the handheld position tracker 60. In this way, the radiation generation unit 2 can be brought into an aligned orientation and/or position relative to the detection unit 6 in a fast, intuitive and reliable way.

Preferably, the fourth sensor unit 62 comprises sensors configured to capture information regarding acceleration and/or inclination of the fourth sensor unit 62 relative to three spatial directions and/or a magnetic field surrounding the fourth sensor unit 62 relative to the three spatial directions. By tracking the acceleration and/or the inclination and/or the magnetic field signals, in particular over time, a processing unit may determine a position and/or inclination and/or movement of the handheld position tracker 60. In another preferred embodiment, the handheld position tracker 60 is configured to be activated by a user, i.e. by pushing the activation button 61, and to be placed onto a patient, in particular onto a body part of the patient to be imaged. By pushing an alignment button 64 on the handheld position tracker 60, the radiation generation unit 2 is centered on the position marked by the handheld position tracker 60 automatically, i.e. the radiation generation unit 2 and the detection unit 6 are brought into a predetermined orientation and/or position relative to each other. Alternatively or additionally, the alignment button 64 is provided at the carriage 21 and/or at the radiation generation unit 2 (not shown). Basically, the alignment button 64 may not necessarily be a button in the narrower sense, but also any another kind of a control element, e.g. a lever, knob or a touch sensitive screen.

Figure 3:
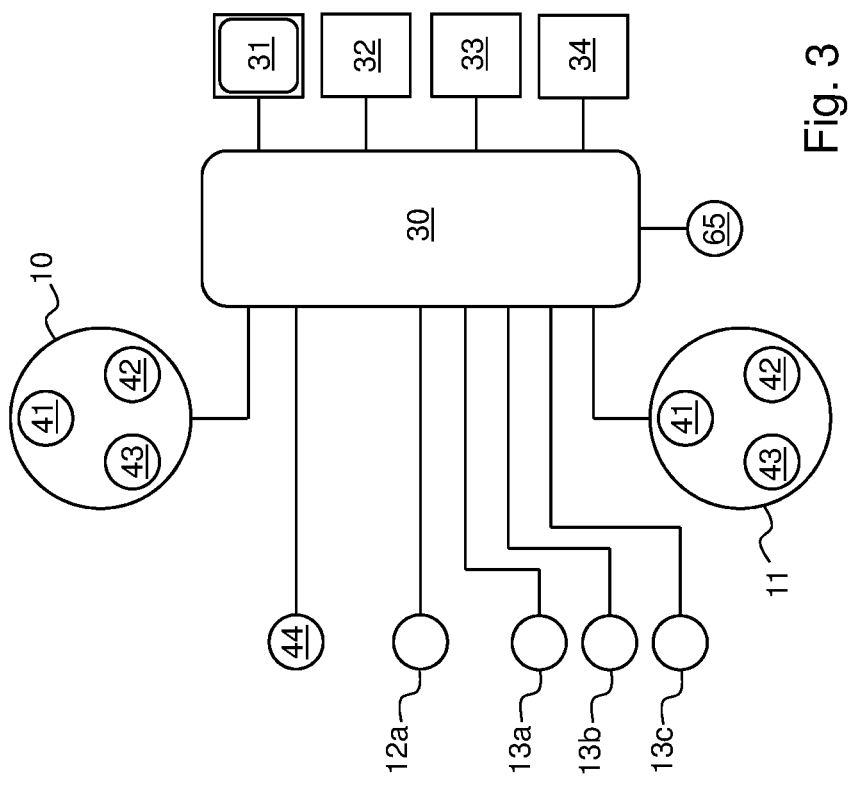
FIG. 3 shows a schematic representation of a first example of a processing unit and components connected to the processing unit.

FIG. 3 shows a schematic representation of an example of a processing unit 30, to which components of the radiation image capturing system are connected, in particular the first sensor unit 10, the second sensor unit 11, the first distance sensor 12a, three second distance sensors 13a, 13b, 13c, an output unit 31, a control element 32, and a drive unit 33. The processing unit 30 is configured to obtain signals and/or information from the sensors and/or sensor units, to process the obtained signals and/or information, to output the processed signals and/or information and/or to further use the obtained and/or processed signals and/or information for controlling the system or components thereof.

Preferably, the first sensor unit 10 and the second sensor unit 11 each comprise an acceleration sensor 41 configured to capture first information, a gyroscope sensor 42 configured to capture second information, and a magnetic field sensor 43 configured to capture third information.

The first information relates to an acceleration of the acceleration sensor 41 with respect to three spatial directions, in particular relative to the gravity vector. If the acceleration sensor 41 is not accelerated by movement, an absolute orientation of the acceleration sensor 41 contained in the first sensor unit 10 and/or the second sensor unit 11 can be determined by the processing unit 30.

The second information relates to an inclination of the gyroscope sensor 42 relative to a predefined axis with respect to three spatial directions, such that a relative orientation of the gyroscope sensor 42 contained in the first sensor unit 10 and/or the second sensor unit 11 can be determined by the processing unit 30.

The third information relates to a magnetic field, in particular an orientation of a magnetic field, in particular the earth's magnetic field, which surrounds the magnetic field sensor 43 with respect to three spatial directions. If the magnetic field is not distorted, e.g. by magnetic fields generated by devices in the vicinity such as motors, the absolute orientation of the magnetic field sensor 43 contained in the first sensor unit 10 and/or the second sensor unit 11 can be determined by the processing unit 30.

Because both of the first sensor unit 10 and the second sensor unit 11 comprise three sources of inclination information each with respect to three spatial directions or spatial axis, the first sensor unit 10 and the second sensor unit 10 may be regarded as nine-dimensional (9D) or 9-axis inclination sensors.

Preferably, the processing unit 30 is configured to determine an orientation of the first sensor unit 10 and/or the second sensor unit 11 and/or an orientation of the radiation generation unit 2 and the detection unit 6 relative to each other based on the first, second and third information. The determined orientation is particularly precise and reliable, because it is based on information captured by three different sensor types. If an inclination measurement by one of the three sensor types is adversely affected, e.g. in case that the acceleration sensor 41 is accelerated by movement or an interfering magnetic field is close to the magnetic field sensor 43, still two of the three sensor types provide correct information or provide necessary information to compensate for effects adversely influencing the inclination measurement of the one sensor.

In a preferred embodiment, the processing unit 30 is configured to further determine the position of the first sensor unit 10 and/or the second sensor unit 11 and/or the radiation generation unit 2 and the detection unit 6, in particular relative to each other, by tracking the changes of first, second and third information provided by the first sensor unit 10 and/or the second sensor unit 11. For example, by tracking the acceleration, in particular the direction of the acceleration, of the acceleration sensor 41 over time, the distance covered by the acceleration sensor 41 and thereby its spatial position can be determined.

Alternatively or additionally, the processing unit 13 is configured to determine a position of the radiation generation unit 2 and the detection unit 6 relative to each other, in particular a distance between them, based on the one or more signals emitted by the first distance sensor 12a and received by the three second distance sensors 13a, 13b, 13c, preferably by also considering the orientation of the radiation generation unit 2 and the detection unit 6 relative to each other which has been determined based on the first, second and third information.

Preferably, the processing unit 30 is configured to determine the distance between the radiation source 3 and the predefined position 14 at the detection unit 6 (see FIGS. 1 and 2) based on position coordinates $[x_p, y_p, z_p]$ of the predefined position 14 in a coordinate system having its origin at the first distance sensor 12a, wherein the position coordinates $[x_p, y_p, z_p]$ of the predefined position 14, which corresponds to the origin of a coordinate system of the detection unit 6, are obtained by the following transformation:

$$\begin{bmatrix} x_p \\ y_p \\ z_p \end{bmatrix} = \overleftrightarrow{\rho}^{-1} \cdot \begin{bmatrix} M_1 \\ M_2 \\ M_3 \end{bmatrix}, \quad (1)$$

wherein $\rho$ is a transformation matrix $$\overleftrightarrow{\rho} = \begin{bmatrix} 1 & \rho_1 & \rho_2 \\ \rho_4 & \rho_5 & \rho_6 \\ \rho_1 & 1 & \rho_3 \end{bmatrix}$$

with components $\rho_1 := r_{11} \cdot r_{12} + r_{21} \cdot r_{22} + r_{31} \cdot r_{32}$;

$\rho_2 := r_{11} \cdot r_{13} + r_{21} \cdot r_{23} + r_{31} \cdot r_{33}$;

$\rho_3 := r_{12} \cdot r_{13} + r_{22} \cdot r_{23} + r_{32} \cdot r_{33}$;

$\rho_4 := (d_1 + d_2 \rho_1)$;

$\rho_5 := (d_2 + d_1 \rho_1)$;

$\rho_6 := (d_1 \rho_2 + d_2 \rho_3)$, wherein the $r_{ij}$ with i=1,2,3 and j=1,2,3 are the components of a transformation (rotation) matrix $$\overleftrightarrow{R} = \begin{bmatrix} r_{11} & r_{12} & r_{13} \\ r_{21} & r_{22} & r_{23} \\ r_{31} & r_{32} & r_{33} \end{bmatrix}$$

for aligning the coordinate system of the sensor unit 6 with the coordinate system of the first distance sensor 12a, and $d_1$ and $d_2$ are components of the position vectors $s^i$ of the three second distance sensors 13a, 13b, 13c in the coordinate system of the detection unit 6 (see FIG. 2):

$$\vec{s}^1 = \begin{bmatrix} d_1 \\ d_2 \\ 0 \end{bmatrix}; \quad \vec{s}^2 = \begin{bmatrix} -d_1 \\ d_2 \\ 0 \end{bmatrix}; \quad \vec{s}^3 = \begin{bmatrix} -d_1 \\ -d_2 \\ 0 \end{bmatrix}..$$

The components of the transformation (rotation) matrix R can be determined by considering the first, second and third information provided by the second sensor unit 11 and, if the first distance sensor 12a is mounted to the radiation generation unit 2, by also considering the first, second and third information provided by the first sensor unit 10, such that the orientation of the radiation generation unit 2 and the detection unit 6 relative to each other can be determined.

If the first distance sensor 12a is mounted to the tube arm 24, as shown in FIG. 2, its coordinate system is fixed such that first, second and third information provided by the first sensor unit 10 does not necessarily have to be considered. Instead, the distance 27 between the radiation source 3 and the first distance sensor 12a is preferably added to the vector coordinates $[x_p, y_p, z_p]$ of the origin of the coordinate system of the detection unit 6.

The coordinates $M_i$ with i=1,2,3 in equation (1) are defined as $$M_1 := \frac{D_1^2 - D_2^2}{4d_1} - d_2;$$

$$M_2 := \frac{D_3^2 - D_1^2}{4};$$

$$M_3 := \frac{D_3^2 - D_2^2}{4d_2} - 4d_1\rho_1;$$

wherein $D_i$ with i=1,2,3 are the measured distances between the first distance sensor 12a and the three second distance sensors 13a, 13b, 13c, for instance by run time measurements of one or more ultrasound signals or summing up the squares of the current/voltage which is induced by one or more magnetic flux signals.

The inverse of $\rho$ can be calculated by $$\overleftrightarrow{\rho}^{-1} = \frac{adj(\overleftrightarrow{\rho})}{\det(\overleftrightarrow{\rho})};$$

wherein $\det(\overleftrightarrow{\rho}) = \rho_1^2 \rho_6 + \rho_4 \rho_4 + \rho_6 - \rho_1 \rho_3 \rho_4 - \rho_1 \rho_5 \rho_2 - \rho_5 \rho_3$ and $$adj(\overleftrightarrow{\rho}) = \begin{bmatrix} [\rho_3 \rho_5 - \rho_6] & [\rho_2 - \rho_1 \rho_3] & [\rho_1 \rho_6 - \rho_2 \rho_5] \\ [\rho_1 \rho_6 - \rho_3 \rho_4] & [-\rho_3 - \rho_1 \rho_2] & [\rho_6 + \rho_2 \rho_4] \\ [\rho_4 + \rho_1 \rho_5] & [\rho_1^2 + 1] & [1\rho_5 - \rho_1 \rho_4] \end{bmatrix}.$$

The processing unit 30 is further configured to output positioning information, i.e. information regarding the orientation and/or position of the radiation generation unit 2 and the detection unit 6, in particular relative to each other, to the user via an output unit 31. The output unit 31 can be designed as a display and/or a speaker such that the positioning information may be provided visually and/or acoustically, respectively.

In a preferred embodiment, the display may show a graphical representation of the radiation generation unit 2 and the detection unit 6 and their relative orientation and/or position such that the user may recognize how to move, i.e. translate and/or rotate, the radiation generation unit 2 and/or the detection unit 6 in order to bring them into an aligned position relative to each other. Alternatively or additionally, the display shows movement instructions on how to bring the radiation generation unit 2 and the detection unit 6 into an aligned position relative to each other by graphically indicating the necessary movement, e.g. by arrows.

In another preferred embodiment, the speaker outputs the positioning information in spoken words addressing the user, who may position the radiation generation unit 2 and/or the detection unit 6 accordingly. Additionally or alternatively, the speaker outputs an audio signal indicating an alignment of the radiation generation unit 2 and the detection unit 6 relative to each other. Preferably, the speaker outputs an audio signal or a series of audio signals whose pitch and/or repetition frequency increases or decreases the closer the radiation generation unit 2 and/or the detection unit 6 come to a preferred alignment relative to each other.

Preferably, the output unit 31 is provided in the vicinity of the handle 23 of the carriage 21 (see FIG. 2), such that the user can access the positioning information output via the output unit 31 while standing behind the carriage 21. Additionally or alternatively, the output unit 31 is provided at the radiation generation unit 2, i.e. at the end of the tube arm 24 opposite to the column 8, such that the user can access the positioning information during an adjustment of the the radiation generation unit 2 relative to a patient and/or the detection unit 6.

The processing unit 30 is further configured to receive movement instructions regarding a desired change in orientation and/or position of the radiation generation unit 2 and the detection unit 6, in particular relative to each other. Preferably, the movement instructions are input by a user via a control element 32. The control element 32 may comprise, e.g., a control stick and/or buttons and/or levers and/or a touch-sensitive display, which is or are configured to be operated by the user according to the desired movement of the mobile carriage 21 and/or the radiation generation unit 2. Alternatively or additionally, the control element 32 comprises a microphone configured to record spoken movement instructions of the user, in particular movement commands for moving the carriage 21, which are processed, i.e. interpreted, by the processing unit 30.

Preferably, the control element 32 is provided in the vicinity of the handle 23, such that the user may input movement instructions when standing behind the carriage 21. Alternatively or additionally, the control element 32 is provided at the radiation generation unit 2, i.e. at the end of the tube arm 24 opposite of the column 8. This allows for altering the orientation of and/or position of the radiation generation unit 2, in particular relative to the detection unit 6, while operating the radiation generation unit 2.

Preferably, the processing unit 30 processes the movement instructions and controls a drive unit 33 accordingly. The drive unit 33 may be a motor, in particular an electric motor, connected to the drive wheels 22b of the mobile carriage 21 (see FIG. 2), such that upon an input of movement instructions by the user, the mobile carriage 21 moves, by translation and/or rotation, across the floor 15.

Alternatively or additionally, the processing unit 30 is configured to control a positioning unit 34 which is configured to move, i.e. translate and/or rotate, the radiation generation unit 2 relative to the carriage 21 and/or the detection unit 2. In particular, a rotation of the column 8 around the first rotation axis 17, a rotation of the second arm element 26 around the second rotation axis 18 and/or a rotation of the radiation generation unit 2 around the third rotation axis 19 may be controlled by the user by inputting according movement instructions via the control element 32. Further, adapting a height of the radiation generation unit 2 relative to the floor 15 by translating the first arm element 25 along the column 8 and/or adjusting a distance between the radiation generation unit 2 and the column 8 by retracting or extending the first part of the first arm element 25 into or out of the second part of the first arm element 25 may be controlled.

As shown in FIG. 3, a third sensor unit 44 may be provided which is configured to provide inclination information on an inclination of the mobile carriage 21. Preferably, this inclination information is also considered by the processing unit 30 when determining the orientation and/or position of the radiation generation unit 2 and the detection unit 6 relative to each other. Further, the information on the inclination of the carriage 21 may be used by the processing unit 30 when controlling the drive unit 33 to move the carriage 21. For instance, the slope of the floor 15 can advantageously be considered in the movement of the carriage 21.

In a preferred embodiment, the processing unit 30 adjusts the power of the drive unit 33 based on the information on the inclination of the mobile carriage 21 provided by the third sensor unit 44 such that the velocity of the carriage 21 is substantially constant regardless whether the carriage 21 moves up a slope or down a slope of the floor 15. Further, the processing unit 30 is preferably configured to control the movement of the carriage 21 such that sharp turns of the carriage 21 are avoided if the carriage 21 is located on a floor 15 having a slope of 5°, that is 9%, or larger.

In another embodiment, the radiation image capturing system 20 comprises a tracking receiver 65 which is configured to receive fourth information captured by the handheld position tracker 60 and wirelessly transmitted by the tracking transmitter 63 (see FIG. 2), e.g via bluetooth or a wireless LAN. In particular, the tracking receiver 65 receives signals emitted by the tracking transmitter 63 comprising information about the translation and/or tilt, in particular the direction of translation and/or tilt, of the handheld position tracker 60. The processing unit 30 is configured to control the drive unit 33 based on the movement information, i.e. to position the carriage 21 such that the radiation generation unit 2 follows the movement performed by the handheld position tracker 60. Alternatively or additionally, the processing unit 30 is configured to control the positioning unit 34 which is configured to rotate the column 8 and/or rotate the second arm element 26 and/or rotate the radiation generation unit 2 and/or extend and/or retract the first arm element 25 and/or translate the tube arm 24 along the column 8, such that the radiation generation unit 2 moves in accordance with the handheld position tracker 60. By this means, the radiation generation unit 2 follows the movement of the handheld position tracker 60, i.e. the hand(s) of the user holding the handheld position tracking 60.

In another preferred embodiment, the tracking transmitter 63 is configured to transmit information regarding acceleration and/or inclination of the fourth sensor unit 62 (shown in FIG. 2) relative to three spatial directions and/or a magnetic field surrounding the fourth sensor unit 62 relative to the three spatial directions. The processing unit 30 controls the drive unit 33 or further drive units (not shown) to move, i.e. translate and/or tilt, the radiation generation unit 2 in accordance with the handheld position tracker 60 based on the information received by the tracking receiver 65.

Figure 4:
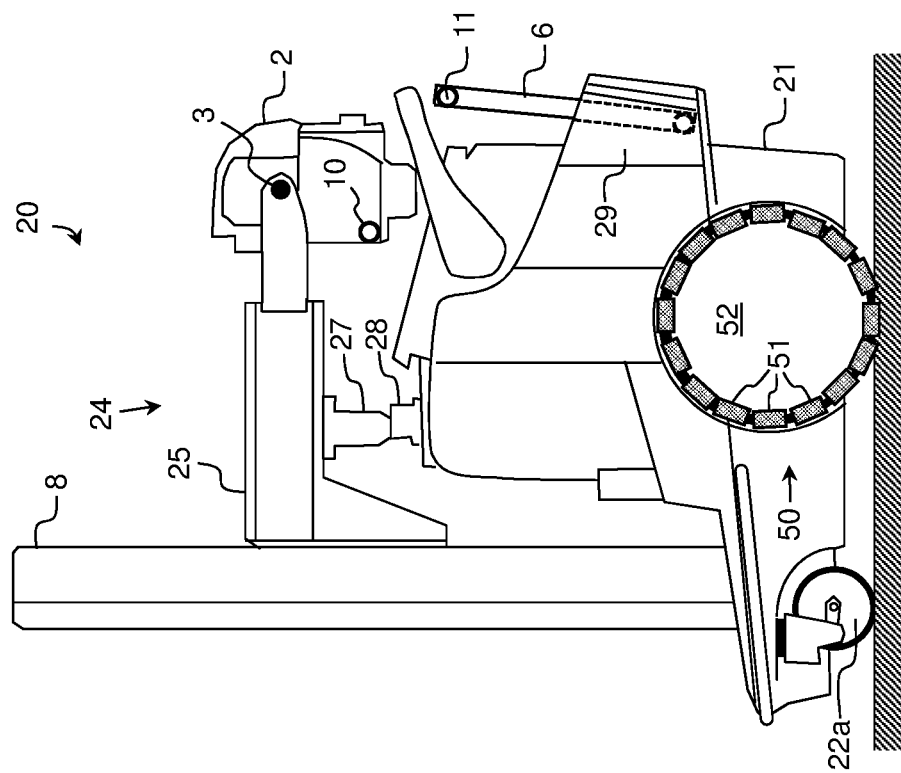
FIG. 4 shows a side view of another example of a radiation image capturing system.

FIG. 4 shows another example of a radiation image capturing system 20, wherein the radiation generation unit 2 is retained in a first reference position and the detection unit 6 is retained in a second reference position. The first reference position corresponds to a position of the radiation generation unit 2 and the tube arm 24, in which the radiation generation unit 2 is arranged essentially parallel to the column 8 such that a straight line running through the radiation source 3 and the center of the aperture 9 is essentially parallel to the column 8 and in which the tube arm 24 is retracted, i.e. where the first part of the first arm element 25 is retracted into the second part of the first arm element 25. Further, in the first reference position, the tube arm 24 is lowered along the column 8 such that a retaining element 27, which is provided at the tube arm 24, rests on and/or is releasably coupled with a support element 28, which is provided at the carriage 21. In the latter case any movement of the radiation generation unit 2 is reliably prevented. In this way, an initial or reference position and/or orientation of the radiation generation unit 2 is defined.

The detection unit 6 is retained in the second reference position by means of a second retaining element 29, e.g. a receptacle into which the detection unit 6 may be inserted such that any movement of the detection unit 6 is reliably prevented. Preferably, the receptacle is a slot into which the detection unit 6 may be fully or partially inserted. In this way, an initial or reference position and/or orientation of the detection unit 6 is defined.

When the radiation generation unit 2 and the detection unit 6 are in their first and second reference position, respectively, their orientation and/or position relative to each other is defined such that the sensors 41, 42, 43 of the first sensor unit 10 and/or the sensors 41, 42, 43 of the second sensor unit 11 can be calibrated (see FIG. 3). This may be done, for example, by capturing calibration values, i.e. first, second and third information of each of the first sensor unit 10 and the second sensor unit 11, and saving it in a memory, in particular in a ring buffer. Preferably, the calibration defines the axis relative to which the gyroscope sensor 42 provides information on a relative inclination. Thus, if the calibration has been performed and the radiation generation unit 2 and/or the detection unit 6 is/are removed from their respective reference position, the processing unit 30 may reliably determine their current orientation and/or position relative to each other based on current first, second and third information provided by the first sensor unit 10 and the second sensor unit 11 and on calibration values read from the ring buffer.

The mobile carriage 21 shown in FIG. 4 comprises one or more omnidirectional wheels 50 by which the maneuverability of the carriage 21 is further enhanced considerably. Preferably, the wheels 50 are configured to allow for sideways and/or diagonal movement of the carriage 21, as exemplarily illustrated in FIG. 5 and described further below. The one or more omnidirectional wheels 50 preferably comprise several rollers 51 arranged at the circumference of a center wheel 52. Each of the rollers 51 is configured to rotate around a respective roller axis (not shown), wherein each of the roller axis is perpendicular to the axis (not shown) of the center wheel 52. In particular, each of the roller axis is essentially tangential to the center wheel 52.

Figure 5:
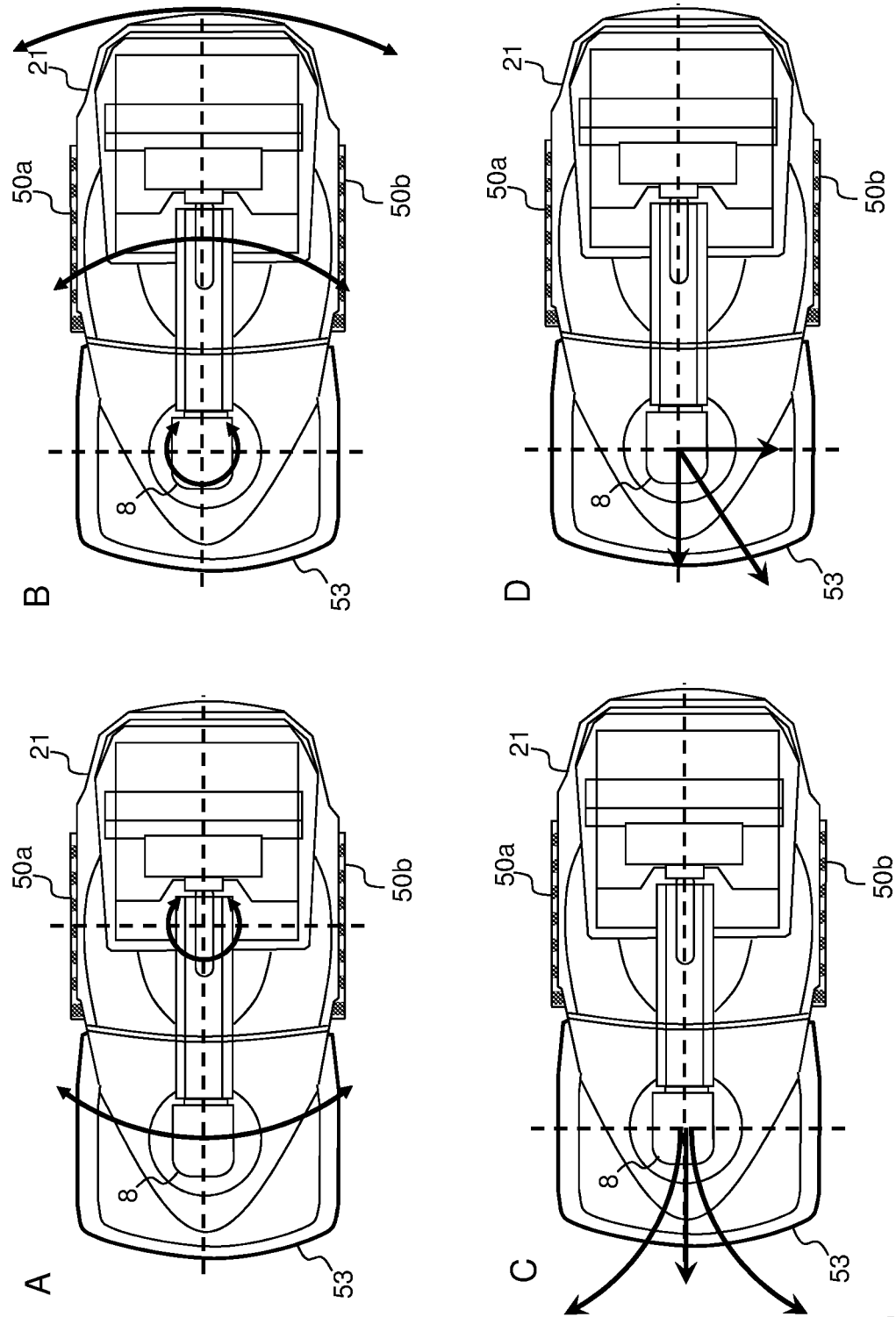
FIGS. 5A to D show top views of another example of a radiation image capturing system in order to illustrate possible movements of the system.

FIG. 5 shows examples of movements of a mobile radiation image capturing system 20 in a top view, wherein the carriage 21 is depicted schematically. By providing the mobile carriage 21 with at least one caster wheel 22a (see FIG. 4) and two omnidirectional wheels 50a, 50b, the carriage 21 may be rotated around different axes as indicated in FIG. 5A and FIG. 5B by curved arrows. Alternatively or additionally, the omnidirectional wheels 50a, 50b may be configured as mecanum wheels (not shown). Further alternatively or additionally, the omnidirectional wheels may be configured as omni wheels with two drives, wherein each of the omni wheels consists of a larger first wheel which is configured for driving a forward movement by rotation around a first main axis and a second smaller wheel which is configured for driving a sideward movement or a rotation of the carriage by rotation around a second main axis, and wherein the first larger wheel and the second smaller wheel are arranged one after another, such that the first main axis and the second main axis are perpendicular to one another and parallel to the floor, respectively (not shown). In FIG. 5A, the center of the rotation lies within the center of mass or in the vicinity thereof of the carriage 21, which is indicated by the intersection point of the two dashed lines. In this case, the carriage 21 essentially rotates in place. In FIG. 5B, the center of the rotation lies within the column 8, which is again indicated by the intersection point of the two dashed lines.

Moreover, the carriage 21 may move in different directions parallel to the floor 15 as indicated in FIG. 5C and FIG. 5D by the curved or straight arrows. In FIG. 5C, if the carriage 21 follows the direction indicated by the curved arrows, the orientation of the carriage 21, i.e. the direction to which the front end 53 of the carriage 21 faces, changes. In FIG. 5D, if the carriage 21 follows the direction of the arrows, the orientation of the carriage 21 does not change, i.e. the carriage 21 may perform a diagonal or sideways motion.

Figure 6:
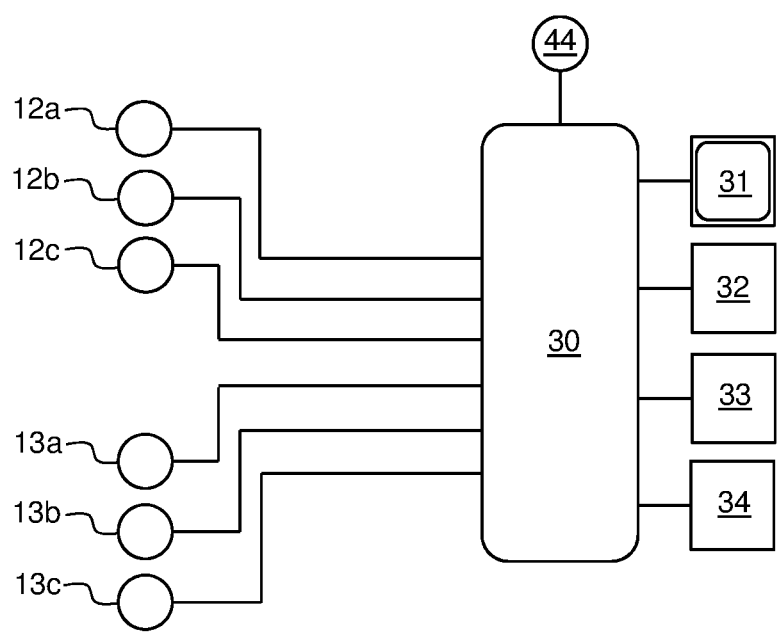
FIG. 6 shows a schematic representation of a second example of a processing unit and components connected to the processing unit.

FIG. 6 shows a schematic representation of a second example of the processing unit 30, to which several components of the radiation image capturing system are connected, in particular three first distance sensors 12a, 12b, 12c, three second distance sensors 13a, 13b, 13c, a third sensor unit 44, an output unit 31, a control element 32, a drive unit 33, and a movement unit 34. The processing unit 30 is configured to obtain signals and/or information from the sensors and/or sensor units, to process the obtained signals and/or information, to output the processed signals and/or information and/or to further use the obtained and/or processed signals and/or information for controlling the system or components thereof.

Moreover, the processing unit 30 is configured to determine the distances between the three first distance sensors 12a, 12b, 12c provided at the radiation generation unit 2 (see FIGS. 1 and 2) and the three second distance sensors 13a, 13b, 13c provided at the detection unit 6 (see FIGS. 1 and 2) based on at least one signal emitted or received by the three first distance sensors 12a, 12b, 12c and received or emitted, respectively, by the three second distance sensors 13a, 13b, 13c. Preferably, the processing unit 30 determines the distance between each of the three first distance sensors 12a, 12b, 12c and each of the three second distance sensors 13a, 13b, 13c, respectively, such that in total nine distances can be determined.

Further, the processing unit 30 is configured to determine the orientation of the radiation generation unit 2 and the detection unit 6 relative to each other based on the determined distances between the three first distance sensors 12a, 12b, 12c and the three second distance sensors 13a, 13b, 13c, in particular by determining the positions of the several distance sensors relative to each other by trilateration based on the determined distances and calculating the relative orientation of the two planes in which the three first distance sensors 12a, 12b, 12c and the three second distance sensors 13a, 13b, 13c are lying.

Preferably, the position, in particular the distance, of the radiation generation unit 2 and the detection unit 6 relative to each other is determined by the processing unit 30 as described above with reference to FIG. 3, wherein the components of the transformation (rotation) matrix R are determined by considering the determined distances between the three first distance sensors 12*a*, 12*b*, 12*c* and the three second distance sensors 13*a*, 13*b*, 13*c*.

Although the three first distance sensors 12*a*, 12*b*, 12*c* and the three second distance sensors 13*a*, 13*b*, 13*c* allow for the determination of nine distances between them, in other embodiments, where more than three first distance sensors 12*a*, 12*b*, 12*c* and more than three second distance sensors 13*a*, 13*b*, 13*c* are provided, more than nine distances may be determined as well. Preferably, the resulting redundancy is used for cross-checking the determined distances between the several distance sensors, and in particular the determined position and/or distance of the radiation generation unit 2 and the detection unit 6 relative to each other. This is particularly advantageous if the at least one signal emitted and received by the several distance sensors is affected by nearby (electro)magnetic sources, e.g. motors, or objects, e.g. body parts of the patient 5 to be imaged.

In another embodiment, the processing unit 30 is configured to determine less than nine, in particular six, distances between the three first distance sensors 12*a*, 12*b*, 12*c* and the three third distance sensors 13*a*, 13*b*, 13*c*.

In another embodiment, the processing unit 30 is further configured to determine the position and/or distance of the radiation generation unit 2 and the detection unit 6 relative to each other based on less than nine, in particular six, distances between the three first distance sensors 12*a*, 12*b*, 12*c* and the three second distance sensors 13*a*, 13*b*, 13*c* and the, in particular fixed, distances between each of the first 12*a*, the second 12*b* and the third 12*c* of the first distance sensors 12*a*, 12*b*, 12*c* and/or the, in particular fixed, distances between each of the first 12*a*, second 12*b* and the third 13*c* of the second distance sensors 13*a*, 13*b*, 13*c*. In particular, the processing unit 30 may be configured in this way even though more than six, in particular nine, distances between the three first distance sensors 12*a*, 12*b*, 12*c* and the three second distance sensors 13*a*, 13*b*, 13*c* are determined. This embodiment is particularly preferable if the determination of some of the more than six, in particular nine, determined distances is influenced by external fields, e.g. generated by motors nearby, or objects located between the several distance sensors hampering the one or more signal emitted and received by the several distance sensors. The same is valid for embodiments with more than three first distance sensors 12*a*, 12*b*, 12*c* and more than three second distance sensors 13*a*, 13*b*, 13*c*, where more than nine distances between the several sensors can be determined.

Regarding further preferred features of the processing unit 30 shown in FIG. 6, the third sensor unit 44, the output unit 30, the control element 32, the drive unit 33 and the movement unit 34, the above elucidations with reference to FIG. 3 apply accordingly.

The invention claimed is:

1. A radiation image capturing system comprising:
a radiation generator that generates X-ray radiation;
a first retainer that accommodates and retains the radiation generator in a first reference position;
a carriage on which the radiation generator is mounted, the carriage being a mobile carriage and/or the radiation generator being movably mounted on the carriage;
at least one detector that captures a radiation image based on the X-ray radiation generated by the radiation generator and transmitted and/or reflected by an object;
a second retainer that accommodates and retains the at least one detector in a second reference position;
a first distance sensor provided at a fixed position relative to the radiation generator and that emits or receives one or more signals, and at least three second distance sensors provided at the at least one detector and each of which receives or emits, respectively, the one or more signals emitted or received, respectively, by the first distance sensor;
a first sensor unit provided at the radiation generator and that provides inclination information regarding an inclination of the radiation generator;
a second sensor unit provided at the at least one detector and that provides inclination information regarding an inclination of the at least one detector; and
a processor configured or programmed to:
determine at least three distances between the first distance sensor provided at the radiation generator and the at least three second distance sensors provided at the at least one detector based on the one or more emitted and received signals;
determine an orientation of the radiation generator and the at least one detector relative to each other based on the inclination information provided by the first sensor unit and the second sensor unit;
determine a position and/or a distance of the radiation generator and the at least one detector relative to each other based on the determined distances between the first distance sensor and the at least three second distance sensors, and on the determined orientation of the radiation generator and the at least one detector relative to each other; and
further determine the orientation of the radiation generator and the at least one detector relative to each other based on:
inclination information provided by the first sensor unit while the radiation generator is retained in the first reference position; and/or
inclination information provided by the second sensor unit while the at least one detector is retained in the second reference position.

2. The radiation image capturing system according to claim 1, wherein
the first sensor unit and the second sensor unit each includes at least one of:
an acceleration sensor that provides first inclination information regarding an acceleration of the acceleration sensor with respect to three spatial directions;
a gyroscope sensor that provides second inclination information regarding an orientation of the gyroscope sensor with respect to the three spatial directions; and
a magnetic field sensor that provides third inclination information regarding a magnetic field surrounding the magnetic field sensor with respect to the three spatial directions; and
the processor is further configured or programmed to determine the orientation of the radiation generator and the at least one detector relative to each other based on at least one of the first inclination information, the second inclination information, and the third inclination information provided by first sensor unit and the second sensor unit.

3. The radiation image capturing system according to claim 2, wherein the first sensor unit and the second sensor unit each includes the acceleration sensor, the gyroscope sensor, and the magnetic field sensor.

4. The radiation image capturing system according to claim 1, wherein the processor is further configured or programmed to:
  determine the distance between the radiation generator and the at least one detector based on a distance between the first distance sensor and a predefined position of the at least one detector; and
  determine the distance between the first distance sensor and the predefined position of the at least one detector based on the determined distances between the first distance sensor and the at least three second distance sensors, and on the determined orientation of the radiation generator and the at least one detector relative to each other.

5. The radiation image capturing system according to claim 4, wherein
  the processor is further configured or programmed to determine the distance between the first distance sensor and the predefined position of the at least one detector based on information regarding a transformation of coordinates of the at least three second distance sensors relative to the predefined position of the at least one detector into coordinates relative to the first distance sensor.

6. The radiation image capturing system according to claim 1, wherein the one or more signals emitted and received by the first distance sensor or the at least three second distance sensors, respectively, include ultrasound signals, magnetic signals, or electromagnetic signals.

7. The radiation image capturing system according to claim 1, wherein
  the processor is further configured or programmed to determine the orientation of the radiation generator and the at least one detector relative to each other based on:
    the inclination information provided by the first sensor unit while the radiation generator is retained in the first reference position and the carriage is not accelerating; and/or
    the inclination information provided by the second sensor unit while the at least one detector is retained in the second reference position and the carriage is not accelerating.

8. The radiation image capturing system according to claim 7, further comprising:
  an output that visually and/or acoustically outputs information; wherein
  the processor is further configured or programmed to:
    determine, based on the orientation and/or the position of the radiation generator and the at least one detector relative to each other, whether the radiation generator and the at least one detector are in an aligned orientation and/or an aligned position relative to each other; and
    when the radiation generator and the at least one detector are not in the aligned orientation and/or the aligned position relative to each other, determine positioning information on how the radiation generator and/or the at least one detector has or have to be moved in order to be in the aligned orientation and/or the aligned position relative to each other, and control the output to output the positioning information.

9. The radiation image capturing system according to claim 8, further comprising:
  a positioner that positions the radiation generator relative to the at least one detector; wherein
  the processor is further configured or programmed to:
    when the radiation generator and the at least one detector are not in an aligned orientation and/or an aligned position relative to each other, control the positioner to position the radiation generator in accordance with the positioning information.

10. A method for operating a radiation image capturing system including a radiation generator that generates X-ray radiation, a first retainer that accommodates and retains the radiation generator in a first reference position, a carriage on which the radiation generator is mounted and the carriage being a mobile carriage and/or the radiation generator is movably mounted on the carriage, at least one detector that captures a radiation image based on X-ray radiation generated by the radiation generator and transmitted and/or reflected by an object, a second retainer that accommodates and retains the at least one detector in a second reference position, a first distance sensor provided at a fixed position relative to the radiation generator, at least three second distance sensors provided at the at least one detector, a first sensor unit provided at the radiation generator, and a second sensor unit provided at the at least one detector, the method comprising the steps of:
  emitting or receiving one or more signals with the first distance sensor, and receiving or emitting, respectively, the one or more emitted or received signals, respectively, with each of the at least three second distance sensors;
  detecting inclination information regarding an inclination of the radiation generator with the first sensor unit;
  detecting inclination information regarding an inclination of the at least one detector with the second sensor unit;
  determining at least three distances between the first distance sensor provided at the radiation generator and the at least three second distance sensors provided at the at least one detector based on the one or more emitted and received signals;
  determining an orientation of the radiation generator and the at least one detector relative to each other based on the inclination information detected by the first sensor unit and the second sensor unit;
  determining a position and/or a distance of the radiation generator and the at least one detector relative to each other based on the determined distances between the first distance sensor and the at least three second distance sensors, and on the determined orientation of the radiation generator and the at least one detector relative to each other; and
  further determining the orientation of the radiation generator and the at least one detector relative to each other based on:
    inclination information provided by the first sensor unit while the radiation generator is retained in the first reference position; and/or
    inclination information provided by the second sensor unit while the at least one detector is retained in the second reference position.

* * * * *

UNITED STATES PATENT AND TRADEMARK OFFICE
CERTIFICATE OF CORRECTION

| | | |
|---|---|---|
| PATENT NO. | : 10,898,156 B2 | Page 1 of 1 |
| APPLICATION NO. | : 16/094290 | |
| DATED | : January 26, 2021 | |
| INVENTOR(S) | : Nebosis et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 134 days.

Signed and Sealed this
Fourteenth Day of February, 2023

Katherine Kelly Vidal
*Director of the United States Patent and Trademark Office*